United States Patent [19]

Sugimori et al.

[11] Patent Number: 4,642,199
[45] Date of Patent: Feb. 10, 1987

[54] NOVEL LIQUID CRYSTAL COMPOUNDS AND LIQUID CRYSTAL COMPOSITIONS CONTAINING SAME

[75] Inventors: Shigeru Sugimori, Fujisawashi; Kazunori Nigorikawa, Yokohamashi, both of Japan

[73] Assignee: Chisso Corporation, Osaka, Japan

[21] Appl. No.: 744,417

[22] Filed: Jun. 13, 1985

[30] Foreign Application Priority Data

Jun. 13, 1984 [JP] Japan .................. 59-121570
Aug. 9, 1984 [JP] Japan .................. 59-166762

[51] Int. Cl.$^4$ .................. C09K 19/34; G02F 1/13; C07D 213/65
[52] U.S. Cl. .................. 252/299.61; 252/299.63; 252/299.64; 350/350 R; 350/350 S; 546/290; 546/300; 546/301; 546/302; 546/303; 546/339; 546/342
[58] Field of Search .................. 252/299.61, 299.63, 252/299.64; 350/350 R, 350 S; 546/290, 300, 301, 302, 303, 339, 342

[56] References Cited

U.S. PATENT DOCUMENTS

| | | | |
|---|---|---|---|
| 4,212,762 | 7/1980 | Dubois et al. .................. | 252/299.64 |
| 4,222,888 | 9/1980 | Dubois et al. .................. | 252/299.64 |
| 4,256,656 | 3/1981 | Beguin et al. .................. | 252/299.61 |
| 4,419,263 | 12/1983 | Praefcke et al. .................. | 252/299.63 |
| 4,480,117 | 10/1984 | Takatsu et al. .................. | 252/299.63 |
| 4,526,704 | 7/1985 | Petrzilka et al. .................. | 252/299.64 |

FOREIGN PATENT DOCUMENTS

| | | | |
|---|---|---|---|
| 0056501 | 7/1982 | European Pat. Off. | |
| 149208 | 7/1985 | European Pat. Off. ........ | 252/299.61 |
| 149238 | 7/1985 | European Pat. Off. ........ | 252/299.61 |
| 3510735 | 10/1985 | Fed. Rep. of Germany .................. | 252/299.61 |
| 54-79185 | 6/1979 | Japan .................. | 252/299.64 |
| 59-80635 | 5/1984 | Japan .................. | 252/299.63 |
| 59-110651 | 6/1984 | Japan .................. | 252/299.63 |
| 59-110652 | 6/1984 | Japan .................. | 252/299.63 |
| 60-163865 | 8/1985 | Japan .................. | 252/299.61 |
| 60-149564 | 8/1985 | Japan .................. | 252/299.61 |
| 2092169 | 8/1982 | United Kingdom ........... | 252/299.61 |
| 2161808 | 1/1986 | United Kingdom ........... | 252/299.61 |

OTHER PUBLICATIONS

Pavluchenko, A. I., et al, J. de Physique, Coll. 3, Supp. No. 4, Tome 40, pp. C3-1-4 (Apr. 1979).
Grebyonkin, M. F., et al, Mol. Cryst. Liq. Cryst., vol. 129, pp. 245-257 (1985).
Schubert, H., Wiss. Z. Univ. Halle XIX'70M, H.5, S. 1-18.
Green, D. C., et al, IBM Tech. Discl. Bull., vol. 15, No. 8, pp. 2467-2468 (Jan. 1973).
Karamysheva, L. A., et al., Mol. Cryst. Liq. Cryst., vol. 67, pp. 241-252 (1981).
Nash, J. A., et al., Mol. Cryst. Liq. Cryst., vol. 25, pp. 299-321 (1974).
Dewar, M. J. S., et al., Liquid Crystals & Ordered Fluids, vol. 2, Plenum Press, N.Y., pp. 733-741 (1980).

*Primary Examiner*—Teddy S. Gron
*Attorney, Agent, or Firm*—Leydig, Voit and Mayer

[57] ABSTRACT

A novel pyridine derivative capable of increasing the dielectric anisotropy value ($\Delta\epsilon$) or optical anisotropy value ($\Delta n$) of liquid crystal compositions including the derivative and lowering the driving voltages of liquid crystal display elements using the composition, and also a liquid crystal composition containing the pyridine derivative are provided, which pyridine derivative is expressed by the formula $$R-X-COO-Y-CH_2CH_2-Z-A$$

wherein R represents an alkyl group or an alkoxy group each of 1-10 carbon atoms; X represents

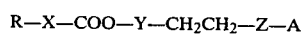

Y represents

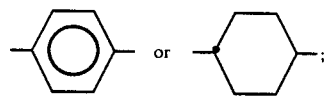

when Y is

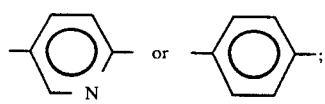

Z represents

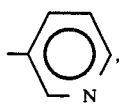

and A represents F, Cl or cyano group; and when Y is

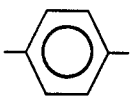

Z represents

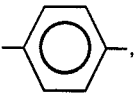

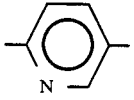

and A represents an alkyl group or an alkoxy group each of 1-10 carbon atoms.

6 Claims, No Drawings

NOVEL LIQUID CRYSTAL COMPOUNDS AND LIQUID CRYSTAL COMPOSITIONS CONTAINING SAME

BACKGROUND OF THE INVENTION

1. Field of the Invention

This invention relates to a novel liquid crystal compound and a liquid crystal composition containing the same.

2. Description of the Prior Art

The display modes of liquid crystal display elements utilizing the optical anisotropy and dielectric anisotropy of liquid crystal compounds include various modes such as those of TN type, DS type, guest-host type, DAP type, White-Tailor type, etc., and the properties required for liquid crystal compounds used vary depending on the respective modes. For example, depending on the kinds of display elements, liquid crystal compounds having a positive dielectric anisotropy value or those having a negative one are required or those having an intermediate value therebetween are suitable. Further, it is necessary for liquid crystal compounds to exhibit liquid crystal phases within a temperature range as broad as possible, and also to be stable to moisture, heat, air, light, etc. At present, however, there is no single compound which satisfies all of such conditions, and several kinds of liquid crystal compounds and if necessary, non-liquid crystal compounds have been blended for practical use.

Recently, liquid crystal display elements operating within a broad temperature range i.e. over a range from low temperatures to high temperatures have come to be required more and more. Further, liquid crystal compositions having a large positive dielectric anisotropy value (hereinafter abbreviated to $\Delta\epsilon$) as a liquid crystal material and capable of a greater reduction in the threshold voltage and saturation voltage required for driving display elements have been desired. Still further, since liquid crystal compositions having a large optical anisotropy value (hereinafter abbreviated to $\Delta n$) can be used in a liquid crystal cell having a reduced distance between the substrates thereof, there is an advantage that the intensity of the electric field applied to the liquid crystal material can be increased even under the same impressed voltage; hence compounds having a large $\Delta n$ have been required.

The object of the present invention is to provide a liquid crystal composition suitable for the above uses and a liquid crystal compound as a component thereof increasing the $\Delta\epsilon$ and $\Delta n$ of the composition.

SUMMARY OF THE INVENTION

The present invention in a first aspect resides in a pyridine derivative expressed by the formula

R—X—COO—Y—CH₂CH₂—Z—A    (I)

wherein R represents an alkyl group or an alkoxy group each of 1~10 carbon atoms; X represents

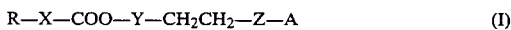

Y represents

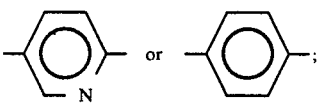

when Y is

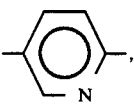

Z represents

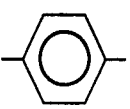

and A represents F, Cl or cyano group; and when Y is

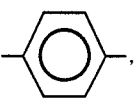

Z represents

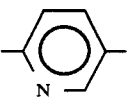

and A represents an alkyl group or an alkoxy group each of 1~10 carbon atoms.

The invention in a second aspect resides in a liquid crystal composition containing at least one member of pyridine derivatives expressed by the above formula (I).

DETAILED DESCRIPTION OF THE PREFERRED EMBODIMENTS

Preferable examples of the compounds of the present invention are the following pyridine derivatives having a linear chain alkyl group or alkoxy group each of 1~10 carbon atoms;

6-[β-(4-cyanophenyl)ethyl]-3-(4-n-alkylbenzoyloxy)-pyridines,
6-[β-(4-cyanophenyl)ethyl]-3-(4-n-alkyloxybenzoyloxy)pyridines,
6-[β-(4-cyanophenyl)ethyl]-3-(trans-4-n-alkylcyclohexylcarbonyloxy)pyridines,
6-[β-(4-fluorophenyl)ethyl]-3-(4-n-alkylbenzoyloxy)-pyridines,
6-[β-(4-fluorophenyl)ethyl]-3-(4-n-alkoxybenzoyloxy)-pyridines, and
6-[β-(4-fluorophenyl)ethyl]-3-(trans-4-n-alkylcyclohexylcarbonyloxy)pyridines, and those having a linear chain alkyl group or alkoxy group each of 3~7 carbon atoms:

6-[4-(trans-4-n-alkylcyclohexylcarbonyloxy)phenethyl]-3-pentyloxypyridines,
6-[4-(4-n-alkylbenzoyloxy)phenethyl]-3-pentyloxypyridines, 6-[4-(4-n-alkoxybenzoyloxy)phenethyl]-3-pentyloxypyridines,
6-[4-(trans-4-n-alkylcyclohexylcarbonyloxy)phenethyl]-3-pentylpyridines,
6-[4-(4-n-alkylbenzoyloxy)phenethyl]-3-pentylpyridines, and
6-[4-(4-n-alkoxybenzoyloxy)phenethyl]-3-pentylpyridines.

Next, the preparation of the compounds of the present invention will be described.

A compound (Ia) of the formula (I) of the present invention wherein Y is

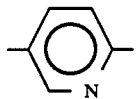

is prepared by first reacting 3-hydroxy-6-methylpyridine (II) with a 4-substituted-benzaldehyde (III) in acetic anhydride solvent, followed by heating the reaction mixture in methanolic hydrochloric acid to obtain a 3-hydroxy-6-[β-(4-substituted-phenyl)vinyl]pyridine (IV), which is then subjected to catalytic reduction with Pd-C catalyst to obtain a 3-hydroxy-6-[β-(4-substituted-phenyl)ethyl]pyridine (V), which is then reacted with a substituted carboxylic acid chloride (VI) in the presence of pyridine to obtain the objective substituted carboxylic acid 6-[β-(4-substituted-phenyl)ethyl]-3-pyridyl ester (Ia).

On the other hand, a compound (Ib) of the formula (I) of the present invention wherein Y is

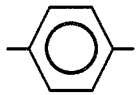

is prepared by first reacting a 3-substituted-6-methylpyridine (VII) with 4-hydroxybenzaldehyde (VIII) in acetic anhydride, followed by heating the reaction mixture in methanolic hydrochloric acid to obtain a 2-[β-(4-hydroxyphenyl)vinyl]-5-substituted-pyridine (IX), which is then esterified with a substituted carboxylic acid chloride (VI) to obtain a substituted-carboxylic acid 4-[β-(5-substituted-2-pyridyl)vinyl]phenyl ester (X), which is then subjected to catalytic reduction to obtain the objective substituted-carboxylic acid 4-[β(5-substituted-2-pyridyl)ethyl]phenyl ester (Ib).

The above preparation steps are shown as follows:

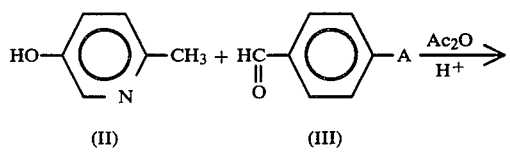

(II)  (III)

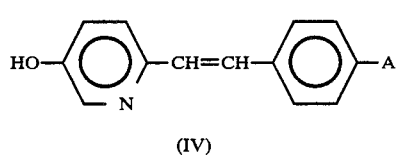

(IV)

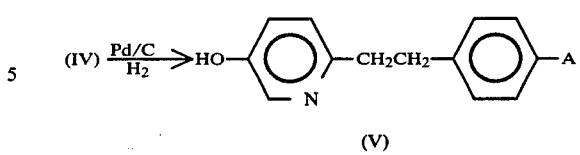

(V)

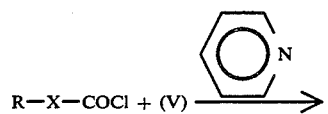

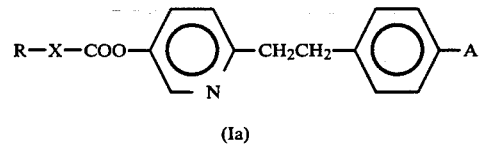

(Ia)

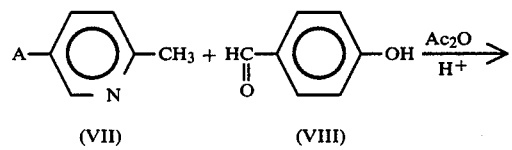

(VII)  (VIII)

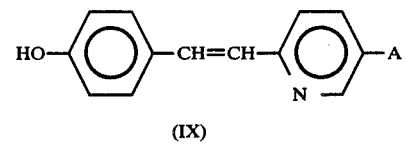

(IX)

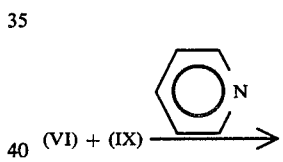

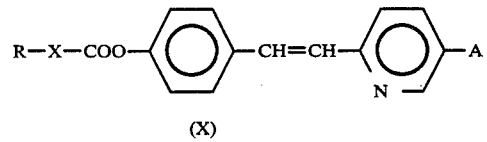

(X)

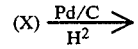

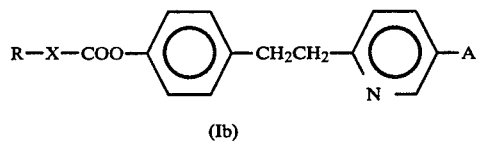

(Ib)

The compounds of the present invention are superior in compatibility with other liquid crystal compounds such as those of esters, Schiff's bases, biphenyls, phenylcyclohexanes, heterocyclic compounds, etc. thereby making it possible to improve various characteristics of liquid crystal compositions having such other liquid crystal compounds blended therein For example, a compound of the formula (I) of the present invention wherein X is

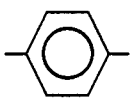

(compound of Example 1 described later) is a liquid crystal compound having a high clearing point and a superior stability, and further having a large positive Δε value of about +33, and also a large Δn value so that it is possible to increase the Δε value and Δn value of liquid crystal compositions obtained by blending the compound with other liquid crystal compounds and also to lower the driving voltage of liquid crystal display elements having the liquid crystal compositions employed therein.

Japanese patent application laid-open No. Sho 54-79185/1979 discloses a liquid crystal compound expressed by the formula

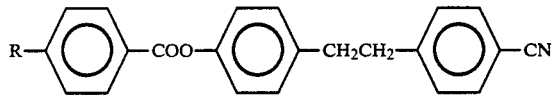

wherein R represents propyl, pentyl, hexyl, heptyl, octyl, methoxy, ethoxy, butoxy, heptyloxy or octyloxy group.

Compounds of the above formula wherein R is hexyl or heptyloxy group have a positive Δε value of about 20. Whereas, 6-[β-(4-cyanophenyl)ethyl]-3-(4-pentylbenzoyloxy)pyridine and 6-[β-(4-cyanophenyl)ethyl]-3-(4-pentyloxybenzoyloxy)pyridine of the present invention exhibit considerably large Δε values of +33.2 and +32.5, respectively. The difference is presumed to be due to the fact that 6-[β-(4-cyanophenyl)ethyl]pyridin-3-yl group has been introduced in place of 4-[β-(4-cyanophenyl)ethyl]phenyl group. Further, even in the case of 6-[β-(4-fluorophenyl)ethyl]-3-(4-pentylbenzoyloxy)pyridine of the present invention wherein the cyano group, having a large effect upon the Δε value, is replaced by a fluoro group, this compound still has a larger Δε value of +25.9 than the above Δε value (+about 20) of the reference. Thus it is evident that introduction of pyridine ring improves the characteristic properties.

The composition of the present invention contains the pyridine derivatives expressed by the formula (I) in 1 to 30% by weight, preferably 5 to 20% by weight. If the content of the pyridine derivatives is less than 1% by weight, the effectiveness of the increase in Δε or Δn of the composition, the lowering of the driving voltage of liquid crystal display elements using the composition, etc. are not notably exhibited. On the other hand, if the content of the pyridine derivatives exceeds 30% by weight, undesirable effects occur such as a rise in the lower limit of the nematic temperatures of the resulting composition, rise in the viscosity of the composition, etc.

Concrete examples of the afore-mentioned liquid crystal compounds other than those expressed by the formula (I), to be blended therewith are as ester liquid crystal compounds, trans-4-alkylcyclohexylcarboxylic acid 4-alkylphenyl esters, trans-4-alkylcyclohexylcarboxylic acid 4-alkoxyphenyl esters, 4-alkoxybenzoic acid 4-alkylphenyl esters, 4-alkylbenzoic acid 4-cyanophenyl esters, 4-(trans-4-alkylcyclohexyl)benzoic acid 4-cyanophenyl esters, etc.; as Schiff's base liquid crystal compounds, 4-alkoxybenzylidene-4-alkanoyloxyanilines, 4-alkoxybenzylidene-4-alkylanilines, 4-alkoxybenzylidene-4-cyanoanilines, etc.; as biphenyl liquid crystal compounds, 4'-alkyl-4-cyanobiphenyls, 4'-alkoxy-4-cyanobiphenyls, 4'-alkoxy-4-alkylbiphenyls, etc.; as phenylcyclohexane liquid crystal compounds, trans-4-alkyl-(4-cyanophenyl)cyclohexanes, trans-4-alkyl-(4-alkoxyphenyl)cyclohexanes, etc.; and as heterocyclic liquid crystal compounds, 5-alkyl-2-(4-cyanophenyl)-1,3-dioxanes, 5-alkyl-2-(4-cyanophenyl)pyrimidines, 5-cyano-2-(4-alkylphenyl)pyrimidines, etc.

Examples of the preferred compositions of the present invention are those consisting of 70 to 99% by weight of trans-4-alkyl-(4-cyanophenyl)cyclohexanes and 30 to 1% by weight of pyridine derivatives expressed by the formula (I), preferably those consisting of 80 to 95% by weight of the former and 20 to 5% by weight of the latter. These compositions have an increased Δε or Δn as shown in Examples mentioned later and the liquid crystal display elements using these compositions have a lowered driving voltage.

The present invention will be described in more detail by way of the following Examples.

EXAMPLE 1

6-[β-(4-cyanophenyl)ethyl]-3-(4-pentyloxybenzoyloxy)pyridine

A mixed solution of 3-hydroxy-6-methylpyridine (3.3 g, 0.03 mol), 4-cyanobenzaldehyde (3.9 g, 0.03 mol) and acetic anhydride (6.1 g, 0.06 mol) was heated under reflux for 25 hours, followed by cooling the reaction mixture, thereafter adding toluene (30 cc), separating the resulting solids by filtration, washing the solids with toluene till the toluene filtrate became colorless, adding methanol (20 cc) and conc. hydrochloric acid (20 cc) to the solids, heating the mixture for 3 hours, cooling, neutralizing with aqueous ammonia, filtering, dissolving the resulting precipitate in ethanol (50 cc), adding Pd-C catalyst (0.3 g), and subjecting the mixture to catalytic reduction at room temperature and the atmospheric pressure. After completion of the reaction, the catalyst was filtered off, followed by distilling off the solvent under reduced pressure and recrystallizing the remaining solids from a mixed solvent of methanol/water (2:1) to obtain 3-hydroxy-6-[β-(4-cyanophenyl)ethyl]pyridine (1.4 g). To this compound were then added toluene (50 cc) and pyridine (3 cc), followed by adding 4-pentoxybenzoyl chloride (1.4 g) to the resulting solution, allowing the mixture to stand overnight, washing with water, then with 2N-hydrochloric acid, further with 2N-NaOH aqueous solution and finally with water till the washing water became neutral, distilling off toluene under reduced pressure and recrystallizing the remaining solids from ethanol to obtain the objective 6-[β-4-(cyanopheny)ethyl]-3-(4-pentyloxybenzoyl)pyridine (0.7 g) having as its phase transition points, a crystalline-nematic point (C-N point) of 107.8°–108.7° C. and a nematic-clearing point (N-I point) of 156.5°–156.8° C.

The following compounds are prepared in a similar manner to the above:
6-[β-(4-cyanophenyl)ethyl]-3-(4-methylbenzoyloxy)pyridine,
6-[β-(4-cyanophenyl)ethyl]-3-(4-ethylbenzoyloxy)pyridine
6-[β-(4-cyanophenyl)ethyl]-3-(4-propylbenzoyloxy)pyridine 6-[β-(4-cyanophenyl)ethyl]-3-(4-butylbenzoyloxy)pyridine
6-[β-(4-cyanophenyl)ethyl]-3-(4-pentylbenzoyloxy)pyridine
  C-N point: 116.6°~117.7° C.
  N-I point: 136.4°~136.6° C.
6-[β-(4-cyanophenyl)ethyl]-3-(4-hexylbenzoyloxy)pyridine
6-[β-(4-cyanophenyl)ethyl]-3-(4-heptylbenzoyloxy)pyridine
6-[β-(4-cyanophenyl)ethyl]-3-(4-octylbenzoyloxy)pyridine
6-[β-(4-cyanophenyl)ethyl]-3-(4-nonylbenzoyloxy)pyridine
6-[β-(4-cyanophenyl)ethyl]-3-(4-decylbenzoyloxy)pyridine
6-[β-(4-cyanophenyl)ethyl]-3-(4-methoxybenzoyloxy)pyridine
6-[β-(4-cyanophenyl)ethyl]-3-(4-ethoxybenzoyloxy)pyridine
6-[β-(4-cyanophenyl)ethyl]-3-(4-propoxybenzoyloxy)pyridine
6-[β-(4-cyanophenyl)ethyl]-3-(4-butoxybenzoyloxy)pyridine
6-[β-(4-cyanophenyl)ethyl]-3-(4-hexyloxybenzoyloxy)pyridine
6-[β-(4-cyanophenyl)ethyl]-3-(4-heptyloxybenzoyloxy)pyridine
6-[β-(4-cyanophenyl)ethyl]-3-(4-octyloxybenzoyloxy)pyridine
6-[β-(4-cyanophenyl)ethyl]-3-(4-nonyloxybenzoyloxy)pyridine
6-[β-(4-cyanophenyl)ethyl]-3-(4-decyloxybenzoyloxy)pyridine
6-[β-(4-cyanophenyl)ethyl]-3-(trans-4-methylcyclohexylcarbonyloxy)pyridine
6-[β-(4-cyanophenyl)ethyl]-3-(trans-4-ethylcyclohexylcarbonyloxy)pyridine
6-[β-(4-cyanophenyl)ethyl]-3-(trans-4-propylcyclohexylcarbonyloxy)pyridine
6-[β-(4-cyanophenyl)ethyl]-3-(trans-4-butylcyclohexylcarbonyloxy)pyridine
6-[β-(4-cyanophenyl)ethyl]-3-(trans-4-pentylcyclohexylcarbonyloxy)pyridine
  C-N point: 99.8°~100.7° C.
  N-I point: 149.9°~150.2° C.
6-[β-(4-cyanophenyl)ethyl]-3-(trans-4-hexylcyclohexylcarbonyloxy)pyridine
6-[β-(4-cyanophenyl)ethyl]-3-(trans-4-heptylcyclohexylcarbonyloxy)pyridine
6-[β-(4-cyanophenyl)ethyl]-3-(trans-4-octylcyclohexylcarbonyloxy)pyridine
6-[β-(4-cyanophenyl)ethyl]-3-(trans-4-nonylcyclohexylcarbonyloxy)pyridine
6-[β-(4-cyanophenyl)ethyl]-3-(trans-4-decylcyclohexylcarbonyloxy)pyridine
6-[β-(4-fluorophenyl)ethyl]-3-(4-methylbenzoyloxy)pyridine
6-[β-(4-fluorophenyl)ethyl]-3-(4-ethylbenxoyloxy)pyridine
6-[β-(4-fluorophenyl)ethyl]-3-(4-propylbenzoyloxy)pyridine
6-[β-(4-fluorophenyl)ethyl]-3-(4-butylbenzoyloxy)pyridine
6-[β-(4-fluorophenyl)ethyl]-3-(4-pentylbenzoyloxy)pyridine
6-[β-(4-fluorophenyl)ethyl]-3-(4-hexylbenzoyloxy)pyridine
6-[β-(4-fluorophenyl)ethyl]-3-(4-heptylbenzoyloxy)pyridine
6-[β-(4-fluorophenyl)ethyl]-3-(4-octylbenzoyloxy)pyridine
6-[β-(4-fluorophenyl)ethyl]-3-(4-decylbenzoyloxy)pyridine
6-[β-(4-fluorophenyl)ethyl]-3-(4-methoxybenzoyloxy)pyridine
6-[β-(4-fluorophenyl)ethyl]-3-(4-ethoxybenzoyloxy)pyridine
6-[β-(4-fluorophenyl)ethyl]-3-(4-propoxybenzoyloxy)pyridine
6-[β-(4-fluorophenyl)ethyl]-3-(4-butoxybenzoyloxy)pyridine
6-[β-(4-fluorophenyl)ethyl]-3-(4-pentyloxybenzoyloxy)pyridine
  C-N point: 91.6°~93.1° C.
  Smectic A-nematic phase transition point (monotropic): 79.9°~80.0° C.
  N-I point: 111.3°~111.5° C.
6-[β-(4-fluorophenyl)ethyl]-3-(4-hexyloxybenzoyloxy)pyridine
6-[β-(4-fluorophenyl)ethyl]-3-(4-heptyloxybenzoyloxy)pyridine
6-[β-(4-fluorophenyl)ethyl]-3-(4-octyloxybenzoyloxy)pyridine
6-[β-(4-fluorophenyl)ethyl]-3-(4-nonyloxybenzoyloxy)pyridine
6-[β-(4-fluorophenyl)ethyl]-3-(4-decyloxybenzoyloxy)pyridine
6-[β-(4-fluorophenyl)ethyl]-3-(trans-4-methylcyclohexylcarbonyloxy)pyridine
6-[β-(4-fluorophenyl)ethyl]-3-(trans-4-ethylcyclohexylcarbonyloxy)pyridine
6-[β-(4-fluorophenyl)ethyl]-3-(trans-4-propylcyclohexylcarbonyloxy)pyridine
6-[β-(4-fluorophenyl)ethyl]-3-(trans-4-butylcyclohexylcarbonyloxy)pyridine
6-[β-(4-fluorophenyl)ethyl]-3-(trans-4-pentylcyclohexylcarbonyloxy)pyridine
  C-N point: 74.8°~76.4° C.
  Smectic B-smectic A phase transition point (monotropic): 64.8°~65.3° C.
  Smectic A-nematic phase transition point (monotropic): 69.0°~69.3° C.
  N-I point: 105.0°~105.6° C.
6-[β-(4-fluorophenyl)ethyl]-3-(trans-4-hexylcyclohexylcarbonyloxy)pyridine
6-[β-(4-fluorophenyl)ethyl]-3-(trans-4-heptylcyclohexylcarbonyloxy)pyridine
6-[β-(4-fluorophenyl)ethyl]-3-(trans-4-octylcyclohexylcarbonyloxy)pyridine
6-[β-(4-fluorophenyl)ethyl]-3-(trans-4-nonylcyclohexylcarbonyloxy)pyridine
6-[β-(4-fluorophenyl)ethyl]-3-(trans-4-decylcyclohexylcarbonyloxy)pyridine.

EXAMPLE 2

6-[4-(Trans-4-pentylcyclohexylcarbonyloxy)phenethyl]-3-pentyloxypyridine

A mixed solution of 3-pentyloxy-6-methylpyridine (3.6 g, 0.02 mol), 4-hydroxybenzaldehyde (2.4 g, 0.02 mol) and acetic anhydride (4.1 g, 0.04 mol) was heated under reflux for 30 hours, followed by cooling the solution, adding a mixed solution of methanol (30 cc) and conc. hydrochloric acid (30 cc), heating the mixture for 3 hours, cooling, neutralizing with aqueous ammonia, extracting with toluene (50 cc), separating the resulting toluene layer, washing with water, and distilling off the toluene under reduced pressure to obtain a concentrate (3.7 g). To this concentrate were added toluene (50 cc) and pyridine (3 cc), followed by dropwise adding to the resulting solution, trans-4-pentylcyclohexanecarboxylic acid chloride (2.2 g, 0.01 mol), allowing the mixture to stand overnight, washing with water, then with 2N-hydrochloric acid, further with 2N-NaOH aqueous solution and finally with water till the washing water became neutral, distilling off toluene under reduced pressure, and recrystallizing the remaining solids from heptane to obtain 6-[4-(trans-4-pentylcyclohexylcarbonyloxy)styryl]-3-pentyloxypyridine (0.8 g), which was then dissolved in toluene (50 cc), followed by adding Pd-C (0.2 g) to the solution, and subjecting the mixture to catalytic reduction at room temperature and the atmospheric pressure. After completion of the reaction, the catalyst was filtered off, followed by distilling off the solvent under reduced pressure and recrystallizing the remaining solids from heptane to obtain the objective 6-[4-(trans-4-pentylcyclohexylcarbonyloxy)phenethyl]-3-pentyloxypyridine (0.4 g), having as phase transition points, a crystalline-smectic point of 67.2°–68.1° C., a smectic A-nematic point of 101.0°–102.0° C. and a N-I point of 131.1°–131.5° C.

The following compounds are prepared in a similar manner to the above:

6-[4-(trans-4-propylcyclohexylcarbonyloxy)phenethyl]-3-pentyloxypyridine
6-[4-(trans-4-butylcyclohexylcarbonyloxy)phenethyl]-3-pentyloxypyridine
6-[4-(trans-4-hexylcyclohexylcarbonyloxy)phenethyl]-3-pentyloxypyridine
6-[4-(trans-4-heptylcyclohexylcarbonyloxy)phenethyl]-3-pentyloxypyridine
6-[4-(4-propylbenzoyloxy)phenethyl]-3-pentyloxypyridine
6-[4-(4-butylbenzoyloxy)phenethyl]-3-pentyloxypyridine
6-[4-(4-pentylbenzoyloxy)phenethyl]-3-pentyloxypyridine
6-[4-(4-hexylbenzoyloxy)phenethyl]-3-pentyloxypyridine
6-[4-(4-heptylbenzoyloxy)phenethyl]-3-pentyloxypyridine
6-[4-(4-propoxybenzoyloxy)phenethyl]-3-pentyloxypyridine
6-[4-(4-butoxybenzoyloxy)phenethyl]-3-pentyloxypyridine
6-[4-(4-pentyloxybenzoyloxy)phenethyl]-3-pentyloxypyridine
6-[4-(4-hexyloxybenzoyloxy)phenethyl]-3-pentyloxypyridine
6-[4-(4-heptyloxybenzoyloxy)phenethyl]-3-pentyloxypyridine
6-[4-(trans-4-propylcyclohexylcarbonyloxy)phenethyl]-3-pentylpyridine
6-[4-(trans-4-butylcyclohexylcarbonyloxy)phenethyl]-3-pentylpyridine
6-[4-(trans-4-pentylcyclohexylcarbonyloxy)phenethyl]-3-pentylpyridine
6-[4-(trans-4-hexylcyclohexylcarbonyloxy)phenethyl]-3-pentylpyridine
6-[4-(trans-4-heptylcyclohexylcarbonyloxy)phenethyl]-3-pentylpyridine
6-[4-(4-propylbenzoyloxy)phenethyl]-3-pentylpyridine
6-[4-(4-butylbenzoyloxy )phenethyl]-3-pentylpyridine
6-[4-(4-pentylbenzoyloxy)phenethyl]-3-pentylpyridine
6-[4-(4-hexylbenzoyloxy)phenethyl]-3-pentylpyridine
6-[4-(4-heptylbenzoyloxy)phenethyl]-3-pentylpyridine
6-[4-(4-propoxybenzoyloxy)phenethyl]-3-pentylpyridine
6-[4-(4-butoxybenzoyloxy)phenethyl]-3-pentylpyridine
6-[4-(4-pentyloxybenzoyloxy)phenethyl]-3-pentylpyridine
6-[4-(4-hexyloxybenzoyloxy)phenethyl]-3-pentylpyridine
6 -[4-(4-heptyloxybenzoyloxy)phenethyl]-3-pentylpyridine

EXAMPLE 3

A liquid crystal mixture (hereinafter abbreviated as mixture A) having a composition consisting of trans-4-propyl-(4'-cyanophenyl)cyclohexane 30% by weight,
trans-4-pentyl-(4'-cyanophenyl)cyclohexane 40% by weight and
trans-4-heptyl-(4'-cyanophenyl)cyclohexane 30% by weight, has a N-I point of 52.1° C., a Δε of +11.2 and a Δn of 0.119.

When this mixture was sealed in a TN cell of 10 μm thick, the resulting liquid crystal cell had a threshold voltage of 1.54 V and a saturation voltage of 2.13 V.

A liquid crystal composition consisting of 85 parts by weight of the mixture A and 15 parts by weight of 6-[β-(4-cyanophenyl)ethyl]-3-(4-pentyloxybenzoyloxy)pyridine of Example 1 of the present invention had a N-I point of 66.0° C., a Δε of +14.4 and a Δn of 0.133, and the threshold voltage and saturation voltage of a liquid crystal cell having used this composition were 1.50 V and 2.06 V, respectively.

EXAMPLE 4

A liquid crystal composition consisting of 85 parts by weight of the liquid crystal mixture A of Example 3 and 15 parts by weight of 6-[β-(4-cyanophenyl)ethyl]-3-(4-pentylbenzoyloxy)pyridine prepared as in Example 1 of the present invention had a N-I point of 62.7° C., a Δε of +14.5 and a Δn of 0.133, and a liquid crystal cell having used this composition had a threshold voltage of 1.50 V and a saturation voltage of 2.07 V. Thus, it was possible to increase the Δn of the liquid crystal composition by applying the present invention and also to lower the driving voltage of liquid crystal display elements having used the composition.

EXAMPLE 5

A liquid crystal composition consisting of 85 parts by weight of the liquid crystal mixture A of Example 3 and 15 parts by weight of 6-[4-(trans-4-pentylcyclohexylcarbonyloxy)phenethyl]-3-pentyloxypyridine prepared in Example 2 of the present invention had a N-I point of 62.3° C., a Δε of +11.0 and a Δn of 0.119. Thus, it was possible to raise the upper limit temperature of the liquid crystal display element, by applying the present invention.

EXAMPLE 6

A liquid crystal composition consisting of 85 parts by weight of the liquid crystal mixture A of Example 3 and 15 parts by weight of 6-[β-(4-fluorophenyl)ethyl]-3-(4-pentyloxybenzoyloxy)pyridine prepared in Example 1 of the present invention had a N-I point of 56.8° C., a Δε of 13.4 and a Δn of 0.125, and the threshold voltage and saturation voltage of a liquid cell having used the composition were 1.47 V and 2.04, respectively. Thus, it was possible to increase the Δn of the liquid crystal composition and also to lower the driving voltage of the liquid crystal display element having used the composition, by applying the composition.

What we claim is:

1. A pyridine derivative expressed by the formula

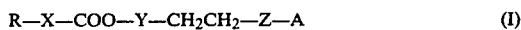

R—X—COO—Y—CH$_2$CH$_2$—Z—A         (I)

wherein R represents an alkyl group or an alkoxy group each of 1~10 carbon atoms; X represents

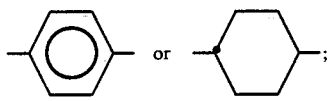

Y represents

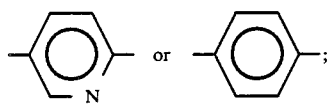

when Y is

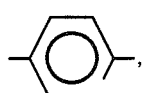

Z represents

and A represents F, Cl or a cyano group; and when Y is

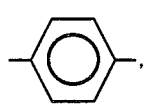

Z represents

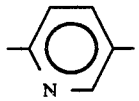

and A represents an alkyl group or an alkoxy group each of 1~10 carbon atoms.

2. A pyridine derivative according to claim 1, expressed by the formula

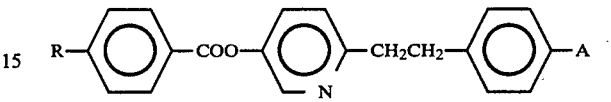

wherein R represents an alkyl group or an alkoxy group each of 1 to 10 carbon atoms and A represents F, Cl or cyano group.

3. A pyridine derivative according to claim 1, expressed by the formula

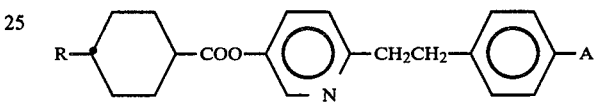

wherein R represents an alkyl group or an alkoxy group each of 1 to 10 carbon atoms and A represents F, Cl or cyano group.

4. A pyridine derivative according to claim 1, expressed by the formula

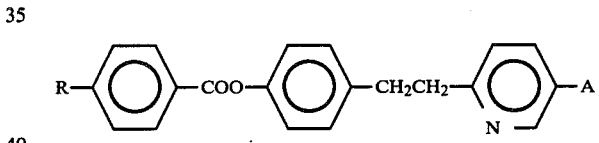

wherein R and A both independently represent an alkyl group or an alkoxy group each of 1 to 10 carbon atoms.

5. A pyridine derivative according to claim 1, expressed by the formula

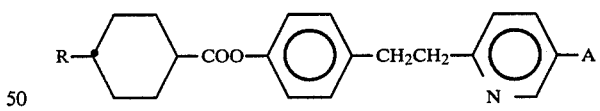

wherein R and A both represent an alkyl group or an alkoxy group each of 1 to 10 carbon atoms.

6. A liquid crystal composition having at least two components at least one of which is selected from the pyridine derivatives set forth in claim 1.

* * * * *